United States Patent
Kim et al.

(10) Patent No.: US 7,565,252 B2
(45) Date of Patent: Jul. 21, 2009

(54) METHOD FOR AUTOMATIC DIFFERENTIATION OF WELD SIGNALS FROM DEFECT SIGNALS IN LONG-RANGE GUIDED-WAVE INSPECTION USING PHASE COMPARISON

(75) Inventors: Sang Young Kim, San Antonio, TX (US); Hegeon Kwun, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 11/634,525

(22) Filed: Dec. 5, 2006

(65) Prior Publication Data

US 2007/0150213 A1    Jun. 28, 2007

Related U.S. Application Data

(60) Provisional application No. 60/742,955, filed on Dec. 6, 2005.

(51) Int. Cl.
*G06F 19/00* (2006.01)
(52) U.S. Cl. ....................................................... 702/35
(58) Field of Classification Search .................... 702/35
See application file for complete search history.

(56) References Cited

U.S. PATENT DOCUMENTS

| | | | |
|---|---|---|---|
| 4,158,964 A | 6/1979 | McCrea et al. |
| 5,591,912 A | 1/1997 | Spisak et al. |
| 6,597,997 B2 | 7/2003 | Tingley |
| 6,751,560 B1 | 6/2004 | Tingley et al. |
| 6,854,332 B2 | 2/2005 | Alleyne |
| 6,917,196 B2 | 7/2005 | Kwun et al. |
| 6,923,067 B2 | 8/2005 | Coen et al. |
| 6,925,881 B1 | 8/2005 | Kwun et al. |
| 2002/0029116 A1 | 3/2002 | Sills et al. |
| 2002/0134161 A1 | 9/2002 | Chinn |

(Continued)

FOREIGN PATENT DOCUMENTS

WO     WO-03/091722 A2 * 11/2003

OTHER PUBLICATIONS

Wilcox, et al., Omnidirectional Guided Wave Inspections . . . , IEEE Transactions on Ultrasonics, Ferroelectrics and Frequency Control, vol. 52, Issue 4, Apr. 2005 pp. 653-662.

(Continued)

*Primary Examiner*—Tung S Lau
(74) *Attorney, Agent, or Firm*—Kammer Browning PLLC (57) ABSTRACT

A method and associated algorithms for identifying and distinguishing geometric feature signals from defect signals in the NDE of longitudinal structures. The method includes the steps of collecting an interrogation signal (including reflected components) from a longitudinal structure under evaluation and comparing it with a selected reference signal from a known geometric feature maintained in a database. The comparison involves a determination of the signals phase. Same phase signals identify the source as a geometric feature, while opposite phase signals identify the source as a defect. The comparison involves the steps of gating each of the signals and creating an array of correlation values between points on each. The correlation values are analyzed and a determination (based on comparing maximum and minimum correlation values) is made of the signal phases. A reliability factor may be determined by comparison of the correlation values and the maximum and minimum thereof.

12 Claims, 6 Drawing Sheets

U.S. PATENT DOCUMENTS

2003/0200809 A1 10/2003 Hatanaka et al.
2004/0216512 A1 11/2004 Kwun et al.

OTHER PUBLICATIONS

Kaftandjian, et al.; The Combined Use of the Evidence Theory . . . ; IEEE Transactions on Instrumentation and Measurement vol. 54, Issue 5, Oct. 2005 pp. 1968-1977.

Jin-Chul Hong, et al., Waveguide Damage Detection by the Matching Pursuit Using . . . , IEEE Ultrasonics Symposium, 2004, vol. 3, Aug. 23-27, 2004 pp. 2310-2313.

Wilcox, A Rapid Signal Processing Technique . . . , IEEE Transactions on Ultrasonics, Ferroelectrics and Frequency Control, vol. 50, Issue 4, Apr. 2003 pp. 419-427.

Legendre, et al., Neural Classification of Lamb Wave Ultrasonic Weld . . . , IEEE Transactions of Instrumentation and Measurement, vol. 50, Issue 3, Jun. 2001 pp. 672-678.

Gachagan, et al., Analysis of Ultrasonic Wave Propagation in Metallic Pipe Structures.., IEEE Ultrasonics Symposium, 2004 pp. 938-941.

* cited by examiner

METHOD FOR AUTOMATIC DIFFERENTIATION OF WELD SIGNALS FROM DEFECT SIGNALS IN LONG-RANGE GUIDED-WAVE INSPECTION USING PHASE COMPARISON

CROSS REFERENCE TO RELATED APPLICATIONS

This application claims the benefit under Title 35 United States Code §119(e) of U.S. Provisional Application No. 60/742,955 filed Dec. 6, 2005, the full disclosure of which is incorporated herein by reference.

BACKGROUND OF THE INVENTION

1. Field of the Invention

The present invention relates generally to methods and devices for the non-destructive evaluation of materials. The present invention relates more specifically to a magnetostrictive sensor based system for the long-range guided-wave inspection of longitudinal structures and a method for automatically differentiating reflected signals from intended geometric elements within the structures (such as welds) from signals generated by unintended geometric features in the structures (such as defects).

2. Description of the Related Art

Introduction

The ongoing ability of structural components to function in their intended manner often depends upon the maintenance of their material integrity. Various techniques are used to investigate and monitor the integrity of longitudinal structural objects. Non-Destructive Evaluation (NDE) techniques are important tools to accomplish this investigation and monitoring. NDE techniques range from ultrasonic testing to electromagnetic (EM)•testing systems and methods. A highly beneficial feature for some NDE techniques is their ability to investigate and monitor a large (especially long) structure from a single or small number of points on the structure. Many such "large structures" are longitudinal in nature (pipes, cables, tubes, plates, and conduits for example). Such structures present specific problems for the investigation and/or monitoring of locations as much as 100 feet from the placement of an NDE type sensor system.

Long-Range Guided-Wave Inspection

Long-range guided-wave inspection of structures is a recently developed NDE inspection method that can examine a long length (such as 100 feet) of structure (such as pipes, tubes, steel cables, and plates) quickly, and therefore economically, from a given sensor location. At present, there are two well established guided-wave inspection technologies. One is referred to commonly as magnetostrictive sensor (MsS) technology, and has been pioneered by Southwest Research Institute (SwRI) of San Antonio, Tex. (SwRI is the Assignee of a series of U.S. Patents covering MsS based Long-Range Guided-Wave Inspection techniques, including U.S. Pat. Nos. 5,456,113, 5,457,994, 5,581,037, 5,767,766, 6,212,944, 6,294,912, 6,396,262, 6,429,650, 6,624,628, 6,917,196, and as well as additional pending patents).

An example of the functionality of MsS Systems, as described above, can be found in U.S. Pat. No. 6,917,196 issued to Kwun et al. on Jul. 12, 2005 entitled Method and Apparatus Generating and Detecting Torsional Wave Inspection of Pipes and Tubes. This patent describes one approach for implementing MsS Techniques for the NDE of pipes or tubes. In this case, a MsS generates guided waves which travel in a direction parallel to the longitudinal axis of the pipe or tube. This is achieved (in this particular sensor system) by using a magnetized ferromagnetic strip pressed circumferentially against the pipe or tube. The guided waves are generated in the strip, are coupled to the pipe or tube, and propagate along its length. Detected guided waves are coupled back to the thin ferromagnetic strip and may include reflected waves representing defects in the pipe or tube.

A second NDE technique used in conjunction with longitudinal structures is commonly referred to as Lamb wave inspection technology. Commercial systems implementing such techniques are marketed under the names Teletest® and Wavemaker®. These systems have been developed by the Imperial College of Science, Technology of Medicine of London, England. These techniques are typified by the system described in U.S. Pat. No. 6,148,672 entitled Inspection of Pipes issued to Crawley et al. on Nov. 21 2000 and assigned to Imperial College of Science, Technology of Medicine. The patent describes an apparatus and a method for inspecting elongate members, especially pipes, using Lamb waves. The apparatus and method provide an axi-symmetric Lamb wave of a single mode in one direction along the pipe. A receiver is provided to receive the Lamb wave after its passage along the pipe and converts the received wave for storage processing and analysis to determine whether or not there are faults present in the pipe. The apparatus includes at least one, and usually several, excitation rings, each having a number of Lamb wave exciters deployed in equiangular spacing and a ring clamping structure whereby each exciter can be pressed with equal force against the surface of the pipe under inspection.

The MsS based systems described above generate and detect guided waves in ferromagnetic materials (such as carbon or alloyed steel) without requiring direct physical contact to the material. The Lamb wave based systems on the other hand, generate and detect guided waves by coupling the waves to an array of piezoelectric sensors in direct physical contact to the material. The MsS is applicable for inspection of various structures including pipes, tubes, plates, and steel cables, whereas the Lamb wave method is primarily for inspection of pipe from the outside. Both technologies are now in commercial use.

The advantages of using the magnetostrictive effect in NDE applications include; (a) the sensitivity of the magnetostrictive sensors, (b) the mobility of the magnetostrictive sensors, (c) the absence of a need to couple the sensor to the material being investigated, (d) the long-range of the mechanical waves in the material under investigation, (e) the ease of implementation, and (f) the low cost of implementation. The use of magnetostrictive sensors (MsS) in the NDE of materials has proven to be very effective in characterizing defects, inclusions, and corrosion within various types of ferromagnetic and non-ferromagnetic structures. Since guided-waves can propagate long distances (typically 100 feet or more) the magnetostrictive sensor technology can inspect a global volume of a structure very quickly. In comparison, other conventional NDE techniques, such as ultrasonics and EMAT current, inspect only the local area around the sensor.

Signal Analysis—Separation of Defect Signals from Geometric Feature Signals

With guided-wave inspection techniques, a pulse of guided-wave of a given frequency and wave mode is launched along the length of a structure, and signals reflected from anomalies in the structure are detected. Anomalies in the structure that cause a wave reflection include defects (such as corrosion wall loss areas and cracks) and geometric features in the structure (such as welds, weld attachments, and clamps). When a long section of structure, such as in a piping network in a refinery, chemical plant, or power-generation plant, is examined using the long-range guided-wave inspection technology, the test data contain signals produced by geometric features as well as those produced by defects (if defects are present in the structure). In order to find defects and to reduce false calls, the signals produced by geometric features must be properly identified and distinguished within the test data.

If the structure under investigation can be visually examined for the locations of geometric features, proper identification of the geometric feature signals in the test data can readily be made. In cases where the section of the structure examined is hidden from view (for instance, the structure is covered with insulation, buried, or is inside another structure), proper identification of geometric feature signals can be very difficult. In these cases, not only could analysis of the test data be time consuming, but data analysis results could be questionable unless confirmed by exposing the hidden section to direct examination.

In order to improve the reliability of the long-range guided-wave inspection results and, at the same time, reduce the time and expense of the data analysis and confirmation, a method that can automatically separate and identify geometric feature signals from defect signals is needed. The invention disclosed below describes a method and algorithms for achieving automated identification and differentiation of geometric feature signals from defect signals.

SUMMARY OF THE INVENTION

In fulfillment of the stated objectives the present invention provides a method that takes advantage of all of the benefits associated with magnetostrictive sensor investigation of longitudinal structures and incorporates steps that allow for the automatic differentiation of the various types of reflected signals that are received in the process. The methodology is based on an ability to characterize reflected waves as having been generated (reflected) by a "step-up" or a "step-down" feature in the longitudinal structure. Reflected waves from step-up type features, where structural thickness increases (abruptly) in the direction of the propagation of the incident wave, will be in the same phase ("in phase" as hereinafter defined as the incident wave. On the other hand, reflected waves from elements within the longitudinal structure associated with step-down (incident wave propagating from a thicker section of the pipe into a thinner section) the reflected wave from the step has the opposite phase ("opposite phase" as hereinafter defined) from the incident wave.

Methods are additionally provided in the present invention to automatically make the above described distinction utilizing gated portions of the signals, interpolating additional data points into the gated wave forms, and calculating correlation values for the corresponding wave forms. Maximum and minimum correlation values are determined and a comparison of the absolute values of these maximum and minimum values will indicate whether the phases of the two signals are the same or are opposite. Finally, the reliability and accuracy of the determination can be measured using an absolute value function of the maximum and minimum correlation values.

DETAILED DESCRIPTION OF THE PREFERRED EMBODIMENTS

Figure 3:
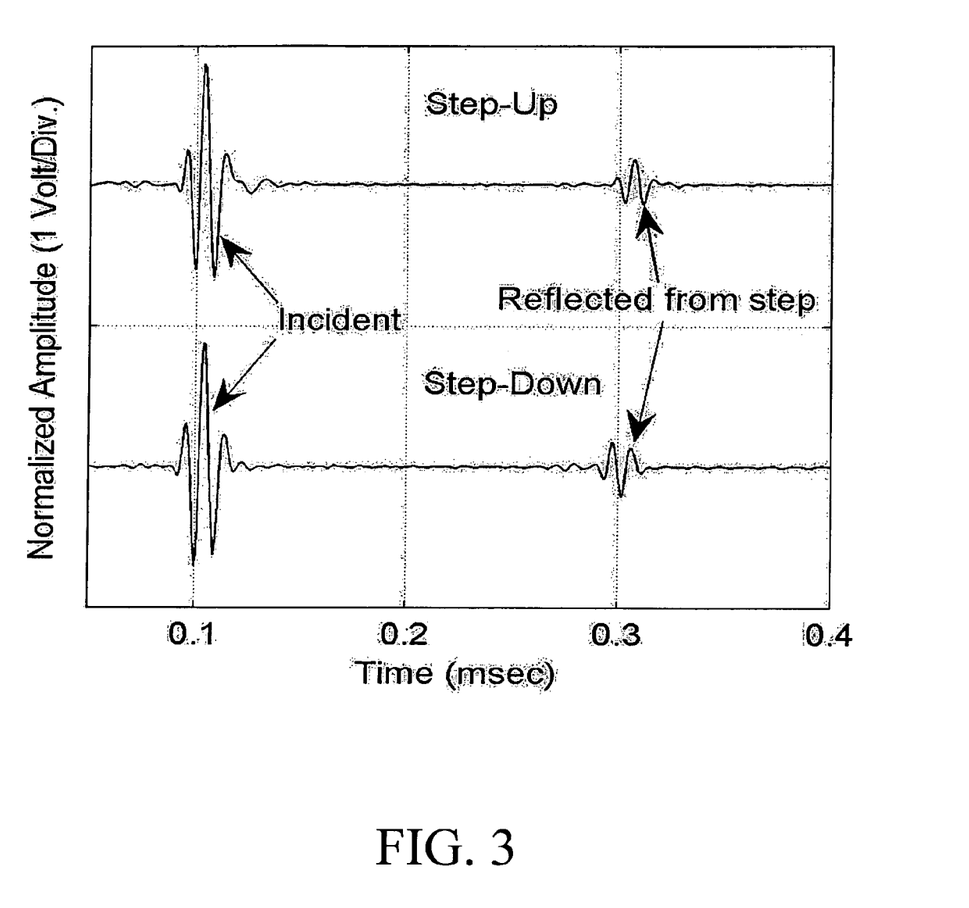
FIG. 3 is a graphic representation of signal amplitudes for both a "step-up" reflective element and a "step-down" reflective element involved in the method of the present invention.

As summarized above, when an incident guided wave propagating along a structure encounters an increased cross-sectional area (for example, welds, weld attachments, and clamps), the wave reflected from that anomaly has the same phase (being "in phase" with) as the incident wave. When the incident wave encounters a decreased cross-sectional area (as in defect locations), the reflected wave has an opposite phase (being "opposite phase" with) to the incident wave. To illustrate the above, the experimentally measured incident waveform in a pipe and the reflected waves from a step-wise change in the pipe wall thickness is shown in FIG. 3. When the wave is propagated from the thinner section of the pipe (the top trace in the figure), the reflected wave from the step has the same phase as the incident wave. When the wave is propagated from the thicker section of the pipe (the bottom trace in the figure), the reflected wave from the step has the opposite phase to the incident wave.

The automatic differentiation of weld signals from defect signals greatly facilitates the data analysis process and minimizes the time and effort required to confirm whether the signal is a weld or a defect. The present invention is particularly useful for cases where a pipeline under inspection (for example) is not readily acceptable for visual examination. Examples of such conditions include lines under insulation, coated lines, lines in casing, and lines at high elevation. The present invention, therefore, is a significant improvement and an extension of the capabilities of the magnetostrictive sensor technology.

By measuring the phase of a reflected wave, therefore, one can identify whether the reflector is a geometric feature (such as a weld, a weld attachment, or a clamp, as examples) or a defect (a wall loss area as an example). The method of the present invention is based on acquiring and analyzing this phase information.

To automate the phase measuring process, the invention uses the following general procedural approach:

(1) Data representing a reference signal is selected from a known geometric feature (such as a weld location or a clamp) such as might be used to calibrate guided-wave signals. (See for example U.S. Pat. No. 6,968,727 issued to Kwun, et al., entitled Calibration Method and Device for Long Range Guided Wave Inspection of Piping).

(2) A comparison is made of the phase of signals of unknown origin with the phase of the signal selected in step (1) above.

(3) If the unknown signal has the same phase as the reference signal, the unknown signal is identified as a geometric feature signal. If the unknown signal has the opposite phase to the reference signal, the unknown signal is identified as a defect signal.

Algorithms used in the methodology of the present invention for automatically comparing the phases and then identifying the nature of the reflector using a computer processing system, include the following steps:

(a) Gate out the reference signal from the test data in such a way that the peak of the signal is at the mid-point of the gate. Typically, the number of data points in the gate is set to 2N, where $$N = \frac{f_s \times (n+1)}{f_c} \quad \text{(Equation 1)}$$

Where $f_s$ is the sampling frequency used to acquire the test data, $f_c$ is the center frequency of the guided wave, and n is the number of cycles in the guided wave pulse.

(b) Gate out a signal from an unknown reflector over 3N data points with the peak of the signal at the mid-point of the gate.

Figure 4A:
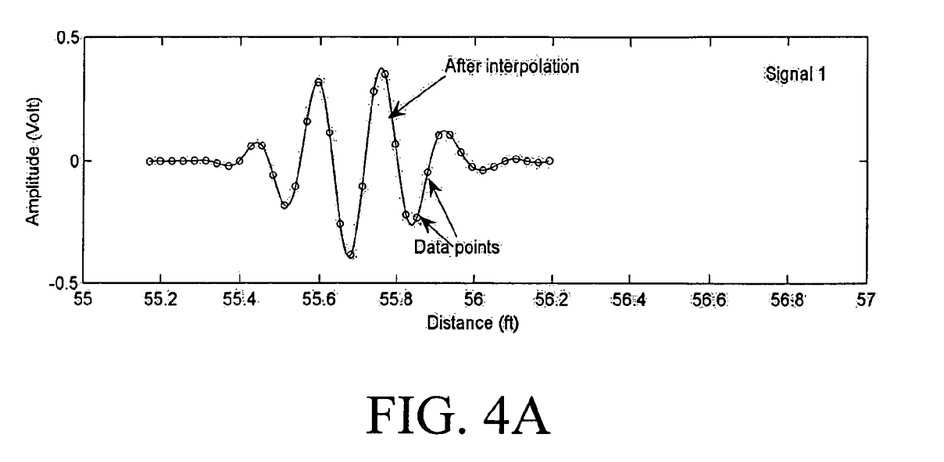
FIG. 4A is a graphic representation of gated reference signal data for phase comparison showing the interpolation of additional points into the plot.
Figure 4B:
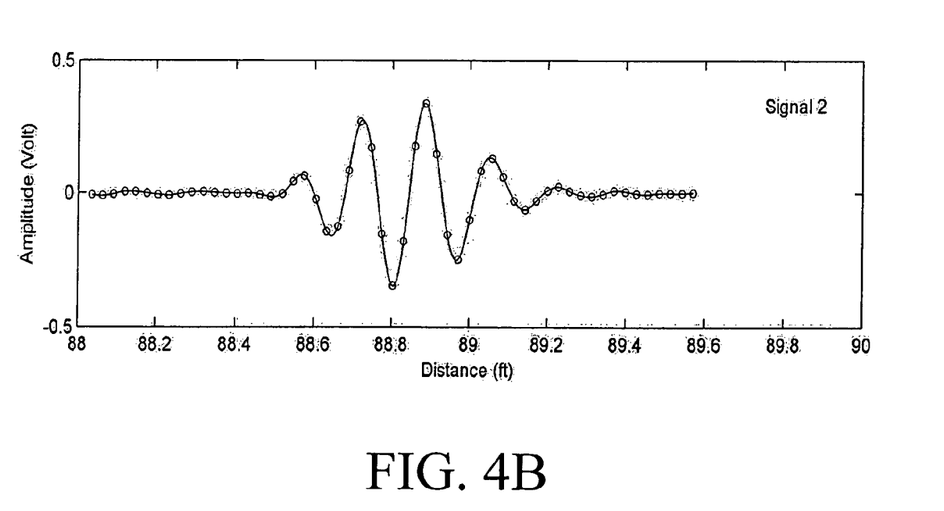
FIG. 4B is a graphic representation of gated unknown reflector signal data for phase comparison showing the interpolation of additional points into the plot.

(c) Increase the number of data points per cycle by interpolating the data points in the gated waveforms (see FIGS. 4A & 4B).

Where $\{x_i^1, y_i^1\}$: x and y values of ith data point in the interpolated reference signal; and $\{x_i^2, y_i^2\}$: x and y values of ith data point in the interpolated unknown reflector signal.

(d) Calculate the correlation values using the following equation:

$$C_j = \sum_{i=1}^{N1} (y_i^1 \times y_{i+j}^2) \text{ for } j = 0 \text{ to } N2 - N1 \quad \text{(Equation 2)}$$

Where N1 is the total number of data points in the reference signal, and N2 is the total number of data points in the unknown reflector signal.

(e) Find the maximum and minimum values of $C_j$:

Where $C1 = \max(C_j)$ and $C2 = \min(C_j)$.

(f) If $|C1| > |C2|$, the phases of two signals are the same (they are defined as being "in phase"). If $|C1| < |C2|$, the phases of two signals are opposite from each other (they are defined as being "opposite phase"). If $|C1| = |C2|$, then the phase comparision is deemed inconclusive.

The reliability of the results of the phase comparison algorithm depends on the quality of the signal from the unknown reflector. For example, whether the signal has good signal-to-noise ratio and whether the signal waveform is distorted are relevant to the reliability of the comparison algorithm.

Based on test results, it has been found that if a factor A, defined as $$A = \text{abs}\left(\frac{|C1| - |C2|}{\sqrt{|C1| \times |C2|}}\right), \quad \text{(Equation 3)}$$

is larger than 0.01, the results of the phase comparison are reliable indicators of the character of the reflector. The above methodology may be carried out according to the system and method described in more detail below.

Figure 1:
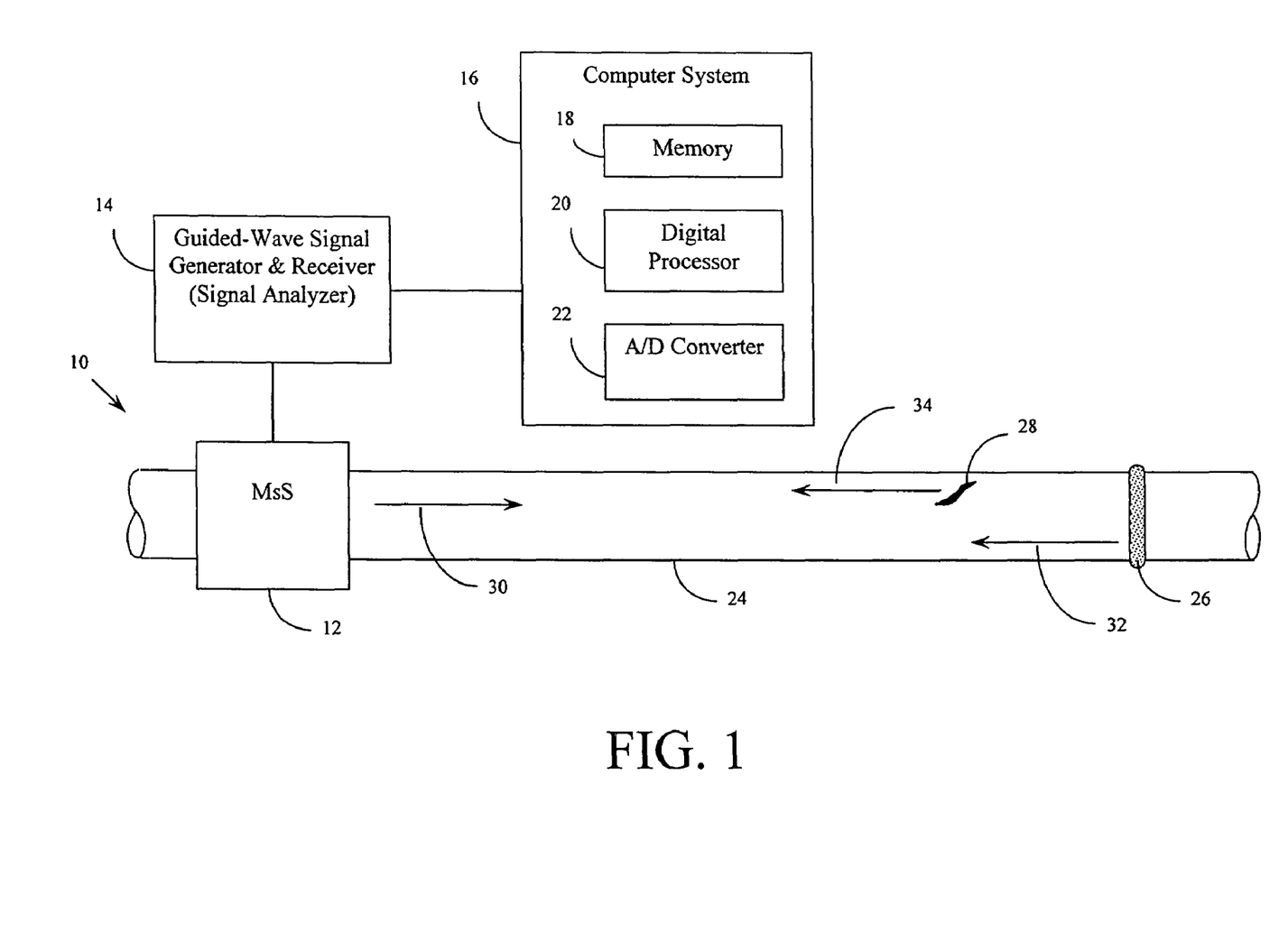
FIG. 1 is a partial schematic diagram showing the primary components of a system appropriate for implementing the method of the present invention.

Reference is made to FIG. 1 for a brief description of a system appropriate for implementing the methodology of the present invention. Long-range guided-wave inspection system 10 is configured to generate guided-waves within the longitudinal structure shown, and to receive back reflected signals from various anomalies and other intended geometrical elements within the longitudinal structure. Inspection system 10 comprises magnetostrictive sensor component 12 positioned in proximity to longitudinal structure 24, which in this instance may be a longitudinal steel pipe or the like. Inspection system 10 further includes guided-wave signal generator 14 which includes the appropriate electronics to drive the magnetostrictive sensor 12 and to thereby generate the guided-waves within the longitudinal structure 24. Also associated with inspection system 10 is computer system 16 generically comprising memory 18, digital processor 20, and analog to digital conversion electronics 22. Suitable data storage components (not shown) may also be relevant for processing methodologies associated with the present invention.

As described in the various magnetostrictive sensor and inspection system patents mentioned above, inspection system 10, by way of magnetostrictive sensor 12 generates guided-waves 30 within longitudinal structure 24. Guided-waves 30 travel along the length and within the material of longitudinal structure 24, until they encounter "anomalous" elements within the structure. These anomalous elements could take the form of intended geometric features, such as weld 26, or could take the form of unintended defect features such as crack 28. In either case, reflected waves, represented as reflected waves 32 and 34, propagate back from these elements and are detected by magnetostrictive sensor component 12 where they are received into the signal analyzer components 14 of the inspection system 10.

Figure 2A:
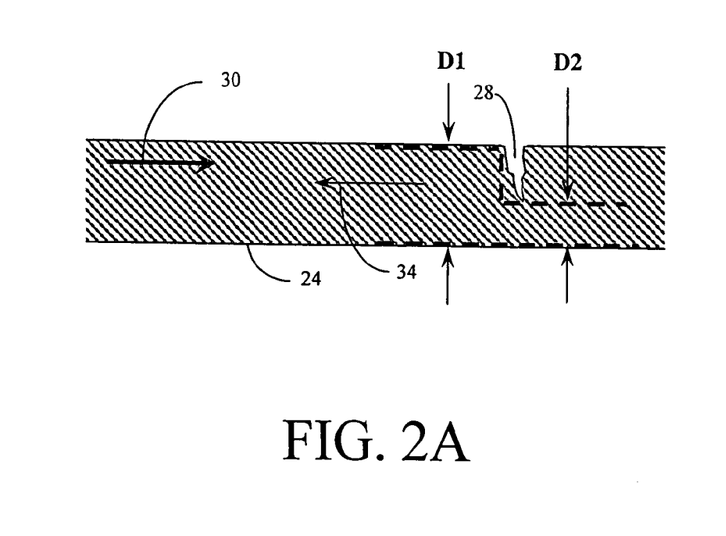
FIG. 2A is a partial cross-sectional view of a pipe wall thickness showing an unintended reflective element (a fatigue crack) of the type detectable and capable of being characterized by the method of the present invention.
Figure 2B:
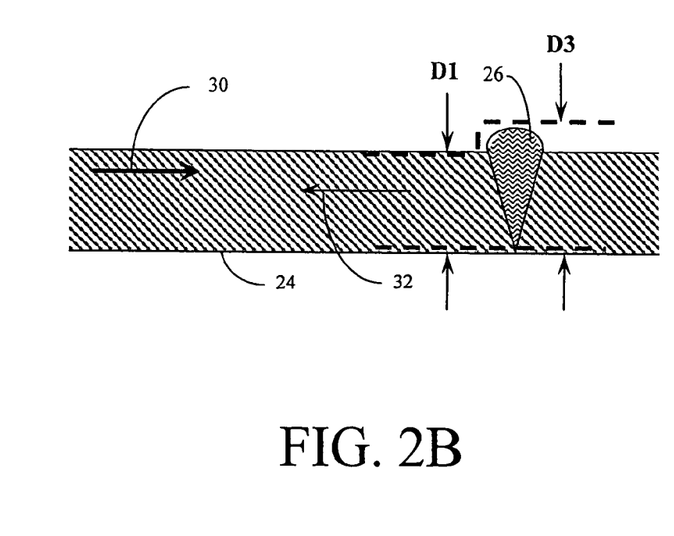
FIG. 2B is a partial cross-sectional view of a pipe wall thickness showing an intended reflective element (a weld) of the type detectable and capable of being characterized by the method of the present invention.

Reference is now made to FIGS. 2A and 2B for a brief description of the detailed configurations of the structures discernable and capable of being characterized by the methodology of the present invention. In FIG. 2A, an inclusion type anomaly is shown, such as a crack formed in the wall of the pipe (longitudinal structure 24) that receives and reflects guided-wave 30. In this cross-sectional view, crack 28 is shown as an inclusion into the wall thickness of pipe 24 in a manner that effectively reduces the wall thickness from D1 to D2. This is the above characterized "step-down" type feature where the propagated wave travels from the thicker section of the pipe into a thinner section.

FIG. 2B, on the other hand, shows what may be characterized as a typical intended geometric anomaly in the pipe wall such as a weld. As shown in FIG. 1, weld 26 is a circumferential weld that might be implemented to connect two pipe sections together. In the cross-sectional view shown in FIG. 2B this weld extends into the typical groove cut for incorporating such welds, but will also typically extend beyond the outer perimeter of the pipe wall (if it is a good weld) in such a manner that increases the effective wall thickness from D1 to D3 as shown. This is the above characterized "step-up" feature where the propagated wave travels from a thinner section of pipe to a point where the effective diameter is thicker.

Reference is now made to FIG. 3 for a graphic representation of the signals associated with the guided-waves in each of the two instances shown in FIGS. 2A and 2B. The upper data plot shown in FIG. 3 represents the signal from a wave propagating from a thinner section of pipe into a thicker section of pipe, as in the so-called step-up change in the pipe wall thickness. In this case it can be seen that the reflected wave from the step has the same phase as the incident wave. In contrast, the lower data plot shown in FIG. 3 which represents the signal from a wave propagating from a thicker section of the pipe into a thinner section (the so-called step-down change) the reflected wave from the step has the opposite phase of the incident wave. A comparison between these two signals for a corresponding point in time (vertical dotted line) indicates this differentiation.

Of course a technician viewing the signals for each of these two types of encountered anomalies might be able to view the signal traces and make a distinction based upon known patterns and identified phase differentiation. It would, however, be preferable to automate the process of identifying phase differentiation for such signals. Reference is now made to FIGS. 4A & 4B, and to FIGS. 5 and 6, for a detailed description of the methodology associated with this automatic comparison of the signal trace phase characteristics and the resultant identification of the signal element as being sourced from an intended anomaly (such as a weld or a clamp) or an unintended anomaly (such as a crack or inclusion).

In FIGS. 4A & 4B, additional data points are shown as being interpolated into the signal data for the reference signal trace (FIG. 4A) and the unknown reflector signal trace (FIG. 4B). The step of interpolating additional points into each of the signal data sets is important in order to acquire a significant number of points to correlate between the signals. This interpolation is carried out according to the algorithm steps described above.

Figure 5A:
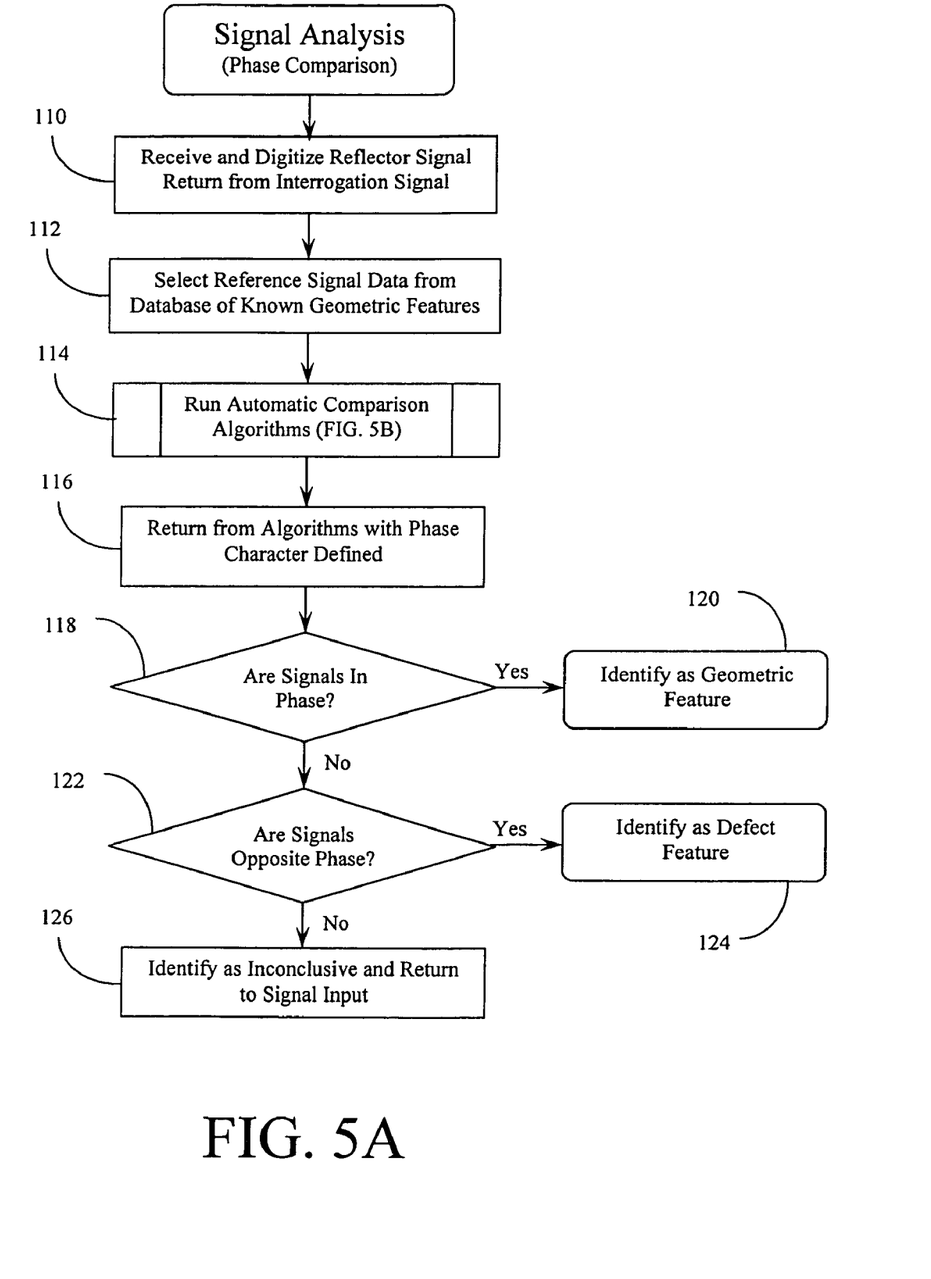
FIG. 5A is a flowchart describing the general steps in the phase comparison method of the present invention.

Reference is now made to FIG. 5A for a description of the methodology of the present invention for determining whether a returned signal indicates an intended geometric discontinuity in the longitudinal structure or an unintended defect in the structure. The methodology is initiated at Step 110 of the Signal Analysis routine wherein the system receives and digitizes the interrogating signal (including reflected components) collected in the manner described above. After receiving the digital information characterizing the interrogating signal (and the reflected return signal components) the process proceeds at Step 112 to the selection of a reference signal for comparison. This reference signal would typically be a previously acquired and confirmed signal stored in a database and retrievable by the system of the present invention. Different reference signal may be compared with the same interrogation signal by repeating the process described herein.

With the interrogation signal data and the reference signal data, the process then proceeds at Step 114 to run the Comparison routine in order to determine whether the signals are in phase or opposite phase in character. The Comparison routine follows the methodology described in more detail below in association with FIG. 5B. Information from the Comparison routine is returned at Step 116 in the form of a definition of the phase character for the interrogation signal as compared to the reference signal. Step 118 queries whether the two signals are in phase and if so, the interrogation signal is identified at Step 120 as a geometric element rather than a defect. If at Step 118 the signals are not characterized as in phase, then at Step 122 it is determined whether the signals were returned as being of opposite phase. If so, then the interrogating signal is identified as a defect at Step 124. If the signals were not identified as opposite in phase, then the signal information is determined to have either been erroneous or inconclusive. If this is the case then at Step 126 the process identifies the signal information as inconclusive and directs the termination of the process or a re-evaluation utilizing new reference signal data.

The comparison process at Step 114 mentioned above is described in more detail in FIG. 5B. The Comparison routine is initiated at Step 130, wherein the signal data (digitized) associated with both the interrogating signal and the selected reference signal are provided for analysis. At Step 132 the reference signal is gated in the manner described above so that the peak of the signal is at the midpoint of the gate. This is followed at Step 134 wherein the interrogation signal (including the unknown reflector component) is also gated over a larger number of data points, but again with the peak of the signal at the midpoint of the gate.

Figure 5B:
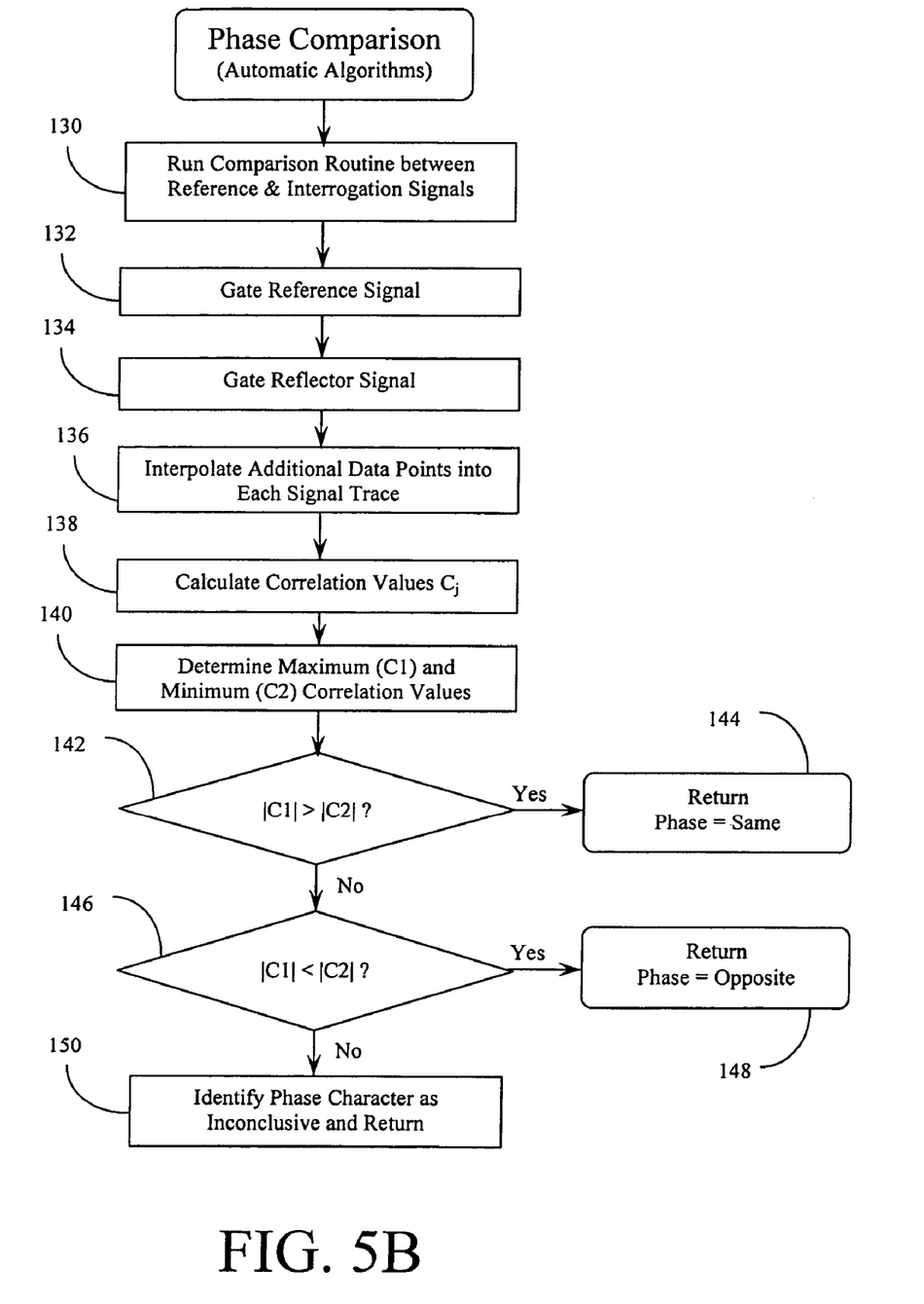
FIG. 5B is a flowchart describing the specific steps in the comparison algorithm of the method of the present invention.

At Step 136 the process carries out an interpolation of additional data points in the gated wave forms, increasing the number of data points per cycle for each of the signals. Then at Step 138 correlation values are determined for selected corresponding data points between the two signal sets of data. At Step 140 a determination is made of the maximum and minimum correlation values based upon the carrying out of Step 138 above. At Step 142 a determination is made whether the absolute value of the maximum correlation value is greater than the absolute value of the minimum correlation value. If this is true, then at Step 144 information is returned that the phases of the two signals are the same. If not, then at Step 146 a determination is made of whether the absolute value of the maximum correlation value is less than the absolute value of the minimum correlation value. If this is the case then at Step 148 information is returned to the effect that the phases of the two signals are opposite from each other. If for some reason neither comparison can be verified, then at Step 150 information is returned to the effect that no conclusive characterization of the phases can be made. The balance of the methodology shown in FIG. 5A is then completed as described above.

In this manner, the present invention provides a method, procedure, and associated steps for automatic identification and differentiation of geometric feature signals from defect signals in signal data associated with long-range guided-wave inspections and monitoring.

Although the present invention has been described in terms of the foregoing preferred embodiments, this description has been provided by way of explanation only, and is not intended to be construed as a limitation of the invention. Those skilled in the art will recognize modifications of the present invention that might accommodate specific non-destructive evaluation environments and structures. Such modifications, as to interrogating signal character, frequency, amplitude, and even sensor configuration, where such modifications are coincidental to the type of structure being investigated, do not necessarily depart from the spirit and scope of the invention.

We claim:

1. A method for distinguishing unintended defect signals from intended geometric structure signals returned from a material undergoing long-range guided-wave inspection, the method comprising the steps of:
   (a) transmitting a guided-wave interrogation signal into the material;
   (b) receiving a guided-wave return signal from a reflector within the material;
   (c) digitizing the return signal from the reflector;
   (d) selecting reference signal data from a database of signal data associated with known intended geometric structures;
   (e) comparing the phase of the return signal with the phase of the reference signal data;

(f) if the return signal and reference signal are in phase, then identifying the return signal as being sourced from an intended geometric structure in the material;

(g) if the return signal and reference signal are opposite phase, then identifying the return signal as being sourced from an unintended defect in the material; and (h) if the return signal and reference signal are neither in phase or opposite phase, then identifying the comparison as inconclusive.

2. The method of claim 1 wherein the step of comparing the phase of the return signal with the phase of the reference signal comprises the steps of:

(a) gating the reference signal data to establish a peak of the signal at a mid-point of the gate;

(b) gating the return signal data to establish a peak of the signal at a mid-point of the gate;

(c) interpolating additional data points into each signal data set;

(d) calculating correlation values for a selection of corresponding data points between the two signal data sets;

(e) determining a maximum correlation value and a minimum correlation value;

(f) comparing the absolute value of the maximum correlation value with the absolute value of the minimum correlation value;

(g) if the absolute value of the maximum correlation value is greater than the absolute value of the minimum correlation value, then characterizing the signals as in phase;

(h) if the absolute value of the maximum correlation value is less than the absolute value of the minimum correlation value, then characterizing the signals as opposite phase; and (i) if the absolute values of the maximum and the minimum correlation values are equal, then characterizing the phase comparison as inconclusive.

3. The method of claim 1 further comprising the step of repeating the method steps with new reference signal data if the comparison is identified as inconclusive.

4. The method of claim 1 further comprising the step of repeating the method steps with new return signal data if the comparison is identified as inconclusive.

5. The method of claim 1 wherein the step of transmitting a guided-wave interrogation signal comprises generating a long-range guided mechanical wave into the material.

6. The method of claim 5 wherein the long-range guided mechanical wave signal is generated by a magnetostrictive sensor positioned in proximity to a ferromagnetic element in mechanical association with the material.

7. The method of claim 1 wherein the step of receiving a guided-wave return signal comprises receiving a long-range guided mechanical wave from a reflector within the material.

8. The method of claim 7 wherein the long-range guided mechanical wave is received by a magnetostrictive sensor positioned in proximity to a ferromagnetic element in mechanical association with the material.

9. The method of claim 2 wherein the step of calculating correlation values comprises calculating the correlation values $C_j$ where $$C_j = \sum_{i=1}^{N1} (y_i^1 \times y_{i+j}^2) \text{ for } j = 0 \text{ to } N2 - N1$$

and where N1 is the number of data points in the reference signal data and N2 is the number of data points in the return signal data.

10. The method of claim 2 wherein the step of gating the reference signal data comprises selecting a number of data points within the gate equal to 2N where, $$N = \frac{f_s \times (n+1)}{f_c},$$

and where $f_s$ is a sampling frequency used to acquire the signal data, $f_c$ is a center frequency of the guided wave, and $n$ is a number of cycles in the guided wave pulse, with the peak of the reference signal at the mid-point of the gate.

11. The method of claim 2 wherein the step of gating the return signal data comprises selecting a number of data points within the gate equal to 3N where, $$N = \frac{f_s \times (n+1)}{f_c},$$

and where $f_s$ is a sampling frequency used to acquire the signal data, $f_c$ is a center frequency of the guided wave, and n is a number of cycles in the guided wave pulse, with the peak of the return signal at the mid-point of the gate.

12. The method of claim 2 further comprising the step of determining a reliability of the results of the phase comparison wherein a reliability factor $$A = \text{abs}\left(\frac{|C1| - |C2|}{\sqrt{|C1| \times |C2|}}\right)$$

and a reliability factor A greater than 0.01 indicates a reliable phase comparison.

* * * * *

UNITED STATES PATENT AND TRADEMARK OFFICE
CERTIFICATE OF CORRECTION

| | |
|---|---|
| PATENT NO. | : 7,565,252 B2 |
| APPLICATION NO. | : 11/634525 |
| DATED | : July 21, 2009 |
| INVENTOR(S) | : Sang Young Kim and Hegeon Kwun |

It is certified that error appears in the above-identified patent and that said Letters Patent is hereby corrected as shown below:

Column 1, Line 6, a GOVERNMENT RIGHTS STATEMENT should appear as follows:

The U.S. Government has a paid-up license in this invention and the right in limited circumstances to require the patent owner to license others on reasonable terms as provided for by the terms of Contract No. DTRS56-03-T-0013 awarded by the Department of Transportation (DOT)

Signed and Sealed this

Fifth Day of January, 2010

David J. Kappos
*Director of the United States Patent and Trademark Office*